Dec.13, 1955 A. SIM Plant Pat. 1,437
CARNATION PLANT
Filed July 13, 1954
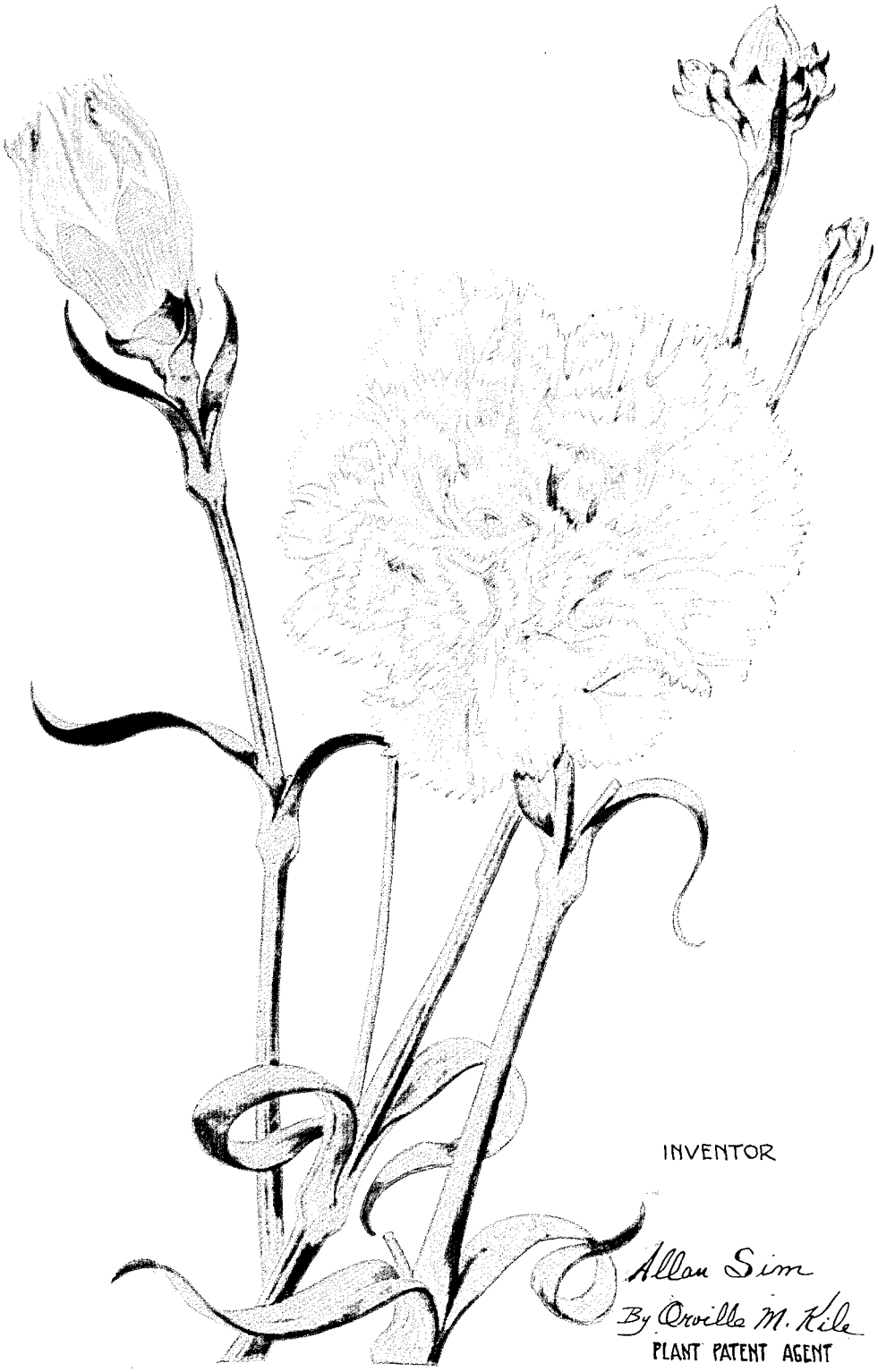
INVENTOR
Allan Sim
By Orville M. Kile
PLANT PATENT AGENT United States Patent Office Plant Pat. 1,437

Patented Dec. 13, 1955

1,437

CARNATION PLANT

Allan Sim, North Berwick, Maine, assignor to Patten & Co., Inc., Tewksbury, Mass.

Application July 13, 1954, Serial No. 443,189

1 Claim. (Cl. 47—60)

My present invention is a new and useful variety of carnation plant of the greenhouse forcing type. It is the result of extensive experimental crosses made by me at the greenhouses in Maine of the nursery company of which I am manager and part owner. It was produced from a cross of the variety William Sim (Plant Patent No. 669) upon another specimen of William Sim.

The new variety resembles the parent variety in many respects but differs particularly in that it has sturdier growth with stronger and longer stems and wider leaves, and a flower that is larger, richer in color and held by a better calyx.

I have reproduced this new variety at our greenhouses by means of cuttings, and its characteristics appear to be permanent.

Accompanying illustrations shown in approximately true colors, a tight bud surrounded by several tiny buds, a partly opened bud, and a fully opened flower of this new variety, together with portions of the stem and foliage.

In the following detailed description, color plate numbers refer to Ridgway's Color Standards and Nomenclature.

THE PLANT

Growth: Vigorous, tall and upright, attaining a height of 4½ to 5 feet. Uniform high quality is maintained throughout the season.

Flowering habit: Very free-flowering.

Stems: Very stronge, stiff and upright. Exceptionally long, with cutting length of approximately 3 feet.

*Nodes.*—Large.

*Internodes.*—About 5 inches long.

*Color.*—Approximately Forest Green (Pl. XVII), covered with gray bloom.

Foliage:

*Quantity.*—Average, although leaves are farther apart than in many varieties.

*Size.*—Average length is 4 to 4½ inches. Width to ½ inch, which is rather wide for carnation foliage.

*Habit.*—Curls moderately.

*Color.*—Same as stems.

THE BLOSSOM

Bud:

*Size.*—Large. When ready to spread, it averages 1¼ inches across at widest point.

*Form.*—Blunt when small, opening broad and full.

*Color.*—Approximately Scarlet Red (Plate I).

*Opening.*—Slow.

Flower:

*Size.*—Very large, averaging 4 to 4½ inches in diameter in the height of the season and under ordinary greenhouse culture.

*Form.*—High-centered, full-petaled. Outer petals larger than center ones. Crinkled rather evenly throughout the flower.

*Color.*—Outer petals are approximately Spectrum Red (Plate I) on inner surface and Scarlet Red (Plate I) on outer surface. Center of flower appears richer and deeper in tone—a color between Spectrum Red and Carmine (Plate I).

*Petalage.*—Very full, averaging 55 to 65 petals.

*Fragrance.*—Mild.

*Calyx.*—Very broad, averaging 1¼ inches across at top and about the same in length. Tough and extremely strong and non-splitting. Approximately Biscay Green (Plate XVII), with points of bracts considerably darker.

*Bracts.*—Strong; same color as stem.

*Longevity.*—Flowers last exceedingly well when cut.

Petals:

*Edge.*—Slightly fringed but not deeply cut. Edge of outer or guard petals is ruffled.

*Size.*—Exposed portion of guard petals is 1½ to 1¾ inches both in width and in length. Shank is 1¼ to 1½ inches long.

*Shape.*—Portion outside calyx is almost round. All but guard petals are folded and bunched.

*Substance.*—Heavy.

*Aspect.*—Slightly velvety both to sight and to touch.

Reproductive organs:

*Pistils.*—Two-pronged. Curved but not curled. Pink-tinged. Long, about 1½ inches above receptacle, extending so as to be visible beyond petals of open flower.

*Stamens.*—Few; white; small and ragged.

*Receptacle.*—Large, containing many seeds.

COMPARISONS

The variety most like my new variety is its parent variety, the subject of Plant Patent No. 669. The two varieties differ principally in the following respects:

1. My new variety has stiffer, stronger and longer stems.
2. My new variety grows more sturdily.
3. The leaves of my new variety are wider.
4. The flower of my new variety has a brighter and richer color.
5. The flower of my new variety is a little larger on the average, and has more petals.
6. The calyx of the flower of my new variety is broader and tougher, enabling it to hold the large flower better without splitting.

Although there appears to be some resemblance of this new variety to the tetraploids known as "Tetra-red" (unpatented) and "Jumbo Sim" (unpatented), a study made of the new variety definitely shows the number of chromosomes as 30, which places it in the class of diploids.

Having thus disclosed my invention, I claim:

The new and distinct variety of carnation plant substantially as herein shown and described, characterized particularly by its sturdy growth; its very tough and non-splitting calyx of large proportions; its wide-leafed foliage; its stiff, strong and unusually long stems; the excellent keeping qualities of its flower; and its large-sized flowers of bright rich red color which is Spectrum Red or darker.

No references cited.